United States Patent [19]

Hoenes et al.

[11] Patent Number: 5,858,691
[45] Date of Patent: Jan. 12, 1999

[54] METHOD AND AGENT FOR THE SIMULTANEOUS COLORIMETRIC AND ELECTROCHEMICAL MEASUREMENT OF AN ANALYTE

[75] Inventors: Joachim Hoenes, Zwingenberg; Holger Kotzan; Volker Unkrig, both of Ladenburg; Michael Marouant, Mannheim, all of Germany

[73] Assignee: Boehringer Mannheim GmbH, Mannheim, Germany

[21] Appl. No.: 663,349

[22] Filed: Jun. 13, 1996

[30] Foreign Application Priority Data

Jun. 13, 1995 [DE] Germany .................. 195 21 019.0

[51] Int. Cl.⁶ ............................................. C12Q 1/26
[52] U.S. Cl. ...................... 435/25; 435/4; 435/26
[58] Field of Search .................. 435/4, 25, 26, 435/805; 422/50, 82.01

[56] References Cited

U.S. PATENT DOCUMENTS

| | | | |
|---|---|---|---|
| 4,629,697 | 12/1986 | Limbach et al. | 435/26 |
| 5,032,506 | 7/1991 | Palmer et al. | 435/26 |
| 5,122,244 | 6/1992 | Hoenes et al. | 204/153.12 |
| 5,200,325 | 4/1993 | Blatt et al. | 435/14 |
| 5,234,818 | 8/1993 | Zimmermann et al. | 435/8 |
| 5,286,362 | 2/1994 | Hoenes et al. | 204/403 |
| 5,457,200 | 10/1995 | Zimmermann et al. | 544/281 |
| 5,484,708 | 1/1996 | Hoenes et al. | 435/14 |

FOREIGN PATENT DOCUMENTS

| | | |
|---|---|---|
| 0 094 161 | 5/1982 | European Pat. Off. . |
| A-0 094 161 | 11/1983 | European Pat. Off. . |
| 32 47 894 | 6/1984 | European Pat. Off. . |
| A-0 127 958 | 12/1984 | European Pat. Off. . |
| A-0 330 517 | 8/1989 | European Pat. Off. . |
| 0 433 854 | 12/1989 | European Pat. Off. . |
| 0 441 222 | 2/1990 | European Pat. Off. . |
| A-0 620 283 | 10/1994 | European Pat. Off. . |
| 43 11 464 | 10/1994 | Germany . |

*Primary Examiner*—José G. Dees
*Assistant Examiner*—Dameron Jones
*Attorney, Agent, or Firm*—Nikaido Marmelstein Murray & Oram LLP

[57] ABSTRACT

The invention concerns a method for the simultaneous colorimetric and electrochemical measurement of an analyte using an oxidizing enzyme and a chromogen A that accepts electrons from the enzyme which is characterized in that the chromogen A after reduction to A' reacts by coupling to a substance BX to form a colored substance A'B the concentratin of which is measured colorimetrically as a measure for the presence or amount of the analyte and in that an electrochemically measurable group $X^-$ is cleaved off during the coupling reaction the concentration of which is measured electrochemically as a measure for the amount of the analyte.

74 Claims, 2 Drawing Sheets

METHOD AND AGENT FOR THE SIMULTANEOUS COLORIMETRIC AND ELECTROCHEMICAL MEASUREMENT OF AN ANALYTE

The invention concerns a method and an agent for the simultaneous colorimetric and electrochemical determination of an analyte using an oxidizing enzyme.

In analytics enzymatic oxidations enable the detection and determination of substances in various sample materials. In this process an oxidizing enzyme acts on an appropriate enzyme substrate in the presence of an electron acceptor which accepts the electrons of the oxidation reaction. In the case of colorimetric detection reactions the electron acceptor is a chromogen which when reduced forms a colour or changes its colour either directly or together with another substance and thus indicates the presence of the enzyme substrate. Colorimetric detection reactions can be evaluated photometrically or also advantageously by visual means and are particularly advantageous at low analyte concentrations. High analyte concentrations above $10^{-4}$M generally produce high changes in absorbance of more than 1 in solution that are difficult to measure and are particularly difficult to measure in the case of reflectance measurements on dry test carriers.

A large number of artificial electron acceptors are known for oxidizing enzymes i.e. for oxidases and dehydrogenases. Examples can for example be found in EP-A-0 330 517.

A further method of determining an analyte using an oxidizing enzyme is electrochemical measurement in which an electrode itself serves as an electron acceptor for the electrons of the enzyme and a corresponding current is measured. Such a method is described for example in EP-A-0 127 958. Electrochemical measurements are particularly suitable for higher analyte concentrations since there is an essentially linear concentration/current relationship.

In EP-A-0 094 161 the detection of an analyte using a PQQ-dependent dehydrogenase and a chromogen as an electron acceptor is described in which the reduction of the chromogen is supposed to be also observed electrochemically. For instructions on how this should be carried out practically, it is merely stated that the concentration change between the reduced and oxidized form of the reducible electron acceptor should be monitored potentiometrically. A simultaneous amperometric measurement is not possible in the case of such a colour formation reaction since the electrons are in principle required either to reduce the chromogen or to reduce the electrode but are not available for both.

There was therefore a need for a combined electrochemical and colorimetric measuring procedure in which colour is formed by reduction of a chromogen and also in which on the other hand a compound which is different from the coloured substance that is formed can also be measured simultaneously either amperometrically or potentiometrically as a measure of the amount of analyte. In this manner it is possible to combine the advantages of a colorimetric measurement with those of an electrochemical measurement and they can complement one another. This is intended above all to result in a uniform accuracy over a particularly large analyte concentration range. The object is achieved by a method and an agent as characterized in the claims.

The invention concerns a method for the simultaneous colorimetric and electrochemical measurement of an analyte using an oxidizing enzyme and a chromogen A which accepts electrons from the enzyme during reduction which is characterized in that the chromogen A, after reduction to A', reacts by coupling with a substance BX to form a coloured substance A'B the concentration of which is measured colorimetrically as a measure for the presence or amount of the analyte and in that an electrochemically measurable group $X^-$ is cleaved during the coupling reaction the concentration of which is measured electrochemically as a measure for the amount of the analyte.

The invention also concerns an agent for the simultaneous colorimetric and electrochemical measurement of an analyte containing an oxidizing enzyme and a chromogen A which accepts electrons from the enzyme during reduction which is characterized in that it contains a substance BX in addition to the chromogen A, the chromogen A being capable of reacting to form a coloured substance A'B after reduction by coupling with the substance BX with cleavage of an electrochemically measurable group $X^-$ in the coupling reaction and in that it additionally contains a sensor electrode for the electrochemical measurement of the amount or concentration of the cleaved group $X^-$.

Figure 1:
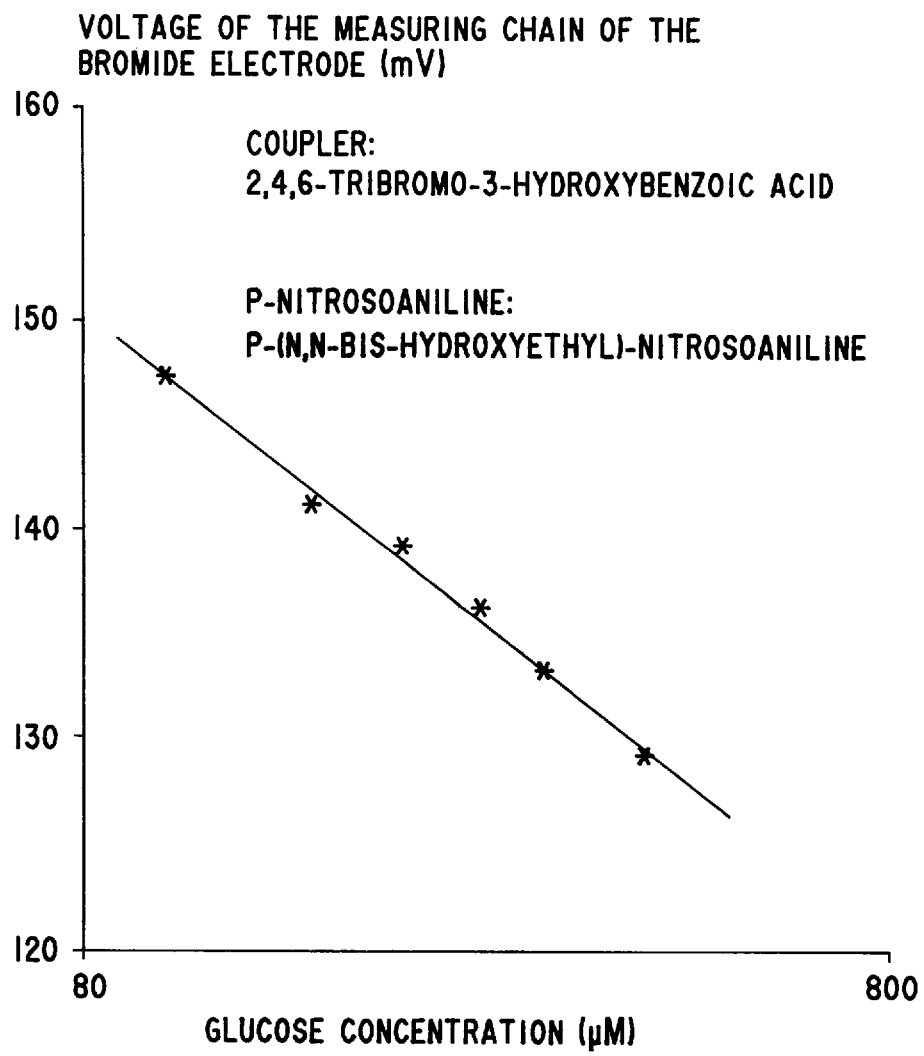
FIG. 1: Glucose-dependent reductive coupling with release of bromide ions. Voltage of the measuring chain of the bromide electrode (mV).

All enzymes come into consideration as the oxidizing enzyme which oxidize an analyte with transfer of electrons onto an artificial substrate A. In this process it is not necessary that the electrons are transferred directly from the enzyme onto the artificial substrate A but rather this can also occur via a mediator such as phenazine methosulfate or diaphorase. An oxidizing enzyme is understood as an oxidoreductase, in particular oxidases, NAD-dependent and PQQ-dependent dehydrogenases; dehydrogenases are particularly preferred.

According to the invention chromogen A is understood to include all substances that after reduction form a compound A' capable of coupling which in turn forms a coloured compound after coupling with a further substance whose maximum absorbance change is in the visible or near infrared range i.e. between 450 and 950 nm.

Imino compounds derived from aromatic compounds are particularly preferred as the reduced compounds A' capable of coupling and in particular quinone diimines such as those described in EP-A-0 620 283 to the complete contents of which reference is hereby made. These are formed by reduction of aromatic nitroso compounds.

Nitrosobenzene derivatives of the general formula I are particularly preferred

(I)

in which $R^1$
  denotes hydrogen, hydroxy, alkyl which is optionally substituted by hydroxy, COOH, $PO_3H_2$, or $SO_3H$, alkoxy, alkylthio, aryloxy, arylthio, halogen or amino which is optionally substituted once or several times by alkyl which is optionally substituted by hydroxy, $PO_3H_2$, dialkyl-phosphinyl, $SO_3H$ or $CO_2H$ and $R^2$ denotes a hydroxy group, alkoxy, aryloxy, arylthio or alkylthio group in which the alkyl residue is optionally in turn substituted by a hydroxy group, an alkoxy group, an amino group which is optionally substituted once or several times by alkyl, $PO_3H_2$, $SO_3H$ or $CO_2H$ as such or in a salt form as an ammonium salt, alkali salt or alkaline earth salt or an amino group $NR^3R^4$ in which $R^3$ and $R^4$ can be the same or different and denote hydrogen, an aryl or alkyl group which in turn can be substituted by a hydroxy, alkoxy, hydroxyalkoxy, an optionally hydroxy-substituted polyalkoxy group $PO_3H_2$, $SO_3H$, COOH as such or in a salt form or an amino group which is substituted once or several times by alkyl or in which $R^3$ and $R^4$ can represent an alkylene residue which is optionally interrupted by oxygen, sulphur or nitrogen wherein nitrogen is substituted by an alkyl, hydroxyalkyl, hydroxyalkoxyalkyl, alkoxyhydroxyalkyl, alkoxycarbonylalkyl, dioxanylylalkyl or polyalkoxyalkyl residue which in turn can each be optionally substituted in the alkyl moiety by a hydroxy residue or if $R^1$ is in the ortho position relative to $NR^3R^4$, $R^3$ or $R^4$ can also represent an alkylene residue together with $R^1$.

In this connection halogen denotes fluorine, chlorine, bromine or iodine. Fluorine and chlorine are particularly preferred.

Alkyl in alkyl, alkoxy or alkylthio denotes a hydrocarbon residue with 1–6 carbon atoms, residues with 1–3 carbon atoms are particularly preferred. The definition given above for alkyl also applies to the alkyl moiety in hydroxyalkyl, dialkylaminoalkyl, hydroxyalkoxyalkyl, alkoxyalkyl, polyalkoxyalkyl, alkoxyhydroxyalkyl and dioxanylyl-alkyl residues. A dioxanylyl-alkyl residue is a residue in which a dioxane ring system is bound to an alkyl residue. This is preferably a 1,4-dioxane ring system i.e.

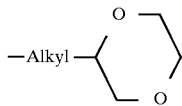

A polyalkoxyalkyl residue is a residue -alkyl-(alkoxy)$_n$-alkoxy in which n=1–10. Preferably n=1–4. Particularly preferably n=1–3. An alkylene residue is a straight-chained or branched—preferably straight-chained—, saturated or unsaturated—preferably saturated—, hydrocarbon chain of 2–5, preferably 2–4 C atoms with two free binding sites.

Aryl in aryl and aralkyl residues is an aromatic ring system containing 6 to 10 carbon atoms of which phenyl is preferred.

Ammonium salts are those which contain the ammonium ion $NH_4^+$ and those which contain ammonium cations substituted once or several times by alkyl, aryl or aralkyl residues.

Alkali salts are preferably those of lithium, sodium or potassium. Alkaline earth salts are preferably those of magnesium or calcium.

Preferred residues $R^1$ are hydrogen and alkyl, in particular hydrogen.

Preferred residues $R^2$ are alkoxy residues and the amino group $NR^3R^4$.

In the meaning of an alkylene residue formed from $R^1$ and $R^3$ interrupted by oxygen, sulphur or nitrogen, a morpholine or thiomorpholine or piperazine residue formed by incorporating the nitrogen atom of the general formula I is preferred. A piperazine residue is particularly preferred.

In the meaning of an alkylene residue formed from $R^1$ and $R^3$ an indoline or 1,2,3,4-tetrahydroquinoline residue formed by incorporating the aromatic ring of the general formula I is preferred.

Preferred salts of a nitrosoaniline derivative according to the invention of the general formula I are in particular those of strong acids, especially mineral acids such as hydrochloric acid, sulphuric acid, nitric acid, phosphoric acid. Hydrochlorides are especially preferred, these are salts of hydrochloric acid.

Preferred nitroso compounds of the general formula I are:
N,N'-bis-(2-hydroxyethyl)-p-nitrosoaniline
N,N'-dimethyl-p-nitrosoaniline
N,N'diethyl-p-nitrosoaniline
N-methyl-N'-(4-nitrosophenyl)-piperazine
N-(2-hydroxyethyl)-5-nitrosoindoline
2,4-dimethoxy-nitrosobenzene
N,N'-bis-(2-methoxyethyl)-4-nitrosoaniline
N-(4-nitrosophenyl)-morpholine
N-(2,2-diethoxy-ethyl)N'-(4-nitrosophenyl)-piperazine
p-nitrosophenol
3-methoxy-4-nitrosophenol Among the electron-rich heteroaromatic nitroso compounds whose aromatic ring system is so rich in electrons that an external +M substituent is not essential for nitroso/oxime tautomerism and for imine formation, pyrazolones and pyrazoles substituted with a nitroso group and especially nitroso-substituted pyrazolo compounds as described for example in Ullmann's Encyclopedia of Industrial Chemistry 5th ed., Vol. A 20, page 72 to 74 are particularly suitable in the method according to the invention. The 3-nitrosopyrazolo compounds of the general formula II are preferred in this case.

Most of these compounds are well-known from the European Patent application EP-A-0 433 854 as precursors for the preparative synthesis of corresponding 3-amino pyrazolo compounds. In formula II:

X—Y denotes $NR^5$—CO or N=$CR^6$ $R^5$ denotes hydrogen, alkyl optionally substituted by hydroxy, carboxy, $SO_3H$, $PO_3H_2$, dialkylphosphinyl $R^6$ denotes hydrogen, alkyl, alkenyl, alkoxy, alkylthio, aryl, arylthio, aralkyl, each optionally substituted by hydroxy, carboxy, $SO_3H$, $PO_3H_2$, a salt of one of these acid residues or/and alkoxycarbonyl; or amino which is optionally substituted by one or two alkyl residues optionally carrying one or several hydroxy, carboxy, or/and alkoxycarbonyl residues wherein in the case that amino is substituted by 2 alkyl residues, these residues can also be closed to form a ring that in addition to the N atom of the amino group can optionally be interrupted also by oxygen, sulphur or a further nitrogen atom, or amino which optionally is substituted by one or two acyl groups, alkoxy or/and aralkoxycarbonyl groups, $H_2N$—CO, alkyl, aralkyl or/and arylcarbamoyl groups; or carboxy, alkoxycarbonyl, carboxamido or halogen and $R^7$ denotes alkyl, thioalkyl or aralkyl optionally substituted by hydroxy, carboxy, $SO_3H$ or $PO_3H_2$ or amino which is optionally substituted by one or two alkyl groups which in turn can be substituted by hydroxy, carboxy, $SO_3H$, dialkylphosphinyl or $PO_3H_2$, wherein at least $R^6$ and/or $R^7$ represents an amino group and R[8] denotes an alkyl or aralkyl group which can optionally be substituted by hydroxy, carboxy, SO$_3$H or PO$_3$H$_2$ or in which R[7] and R[8] together denote a saturated or unsaturated chain with 3 or 4 members of nitrogen atoms or of carbon atoms and optionally one or several nitrogen or sulphur atoms in which carbon atoms are optionally substituted by alkyl, alkoxy, alkylthio, hydroxy, aralkyl, aryl, carboxy, carboxamido, alkoxycarbonyl, cyano, halogen, amino which is optionally substituted by one or two alkyl residues optionally carrying one or several hydroxy, carboxy, or/and alkoxycarbonyl residues and in which nitrogen atoms that are not bound via a double bond are substituted by alkyl or aralkyl optionally substituted by hydroxy, SO$_3$H, PO$_3$H$_2$, carboxy or dialkylphosphinyl or two neighbouring chain substituents optionally form an alkylene group which in turn is optionally substituted with aryl or is anellated as well as, optionally, corresponding tautomeric forms and salts thereof.

In this connection "alkyl"—also as used in alkylthio, dialkylphosphinyl, alkylcarbamoyl and aralkyl residues—denotes a straight-chained or branched alkyl residue with 1–6, preferably 1–4 C atoms. Examples are the methyl, ethyl, propyl, iso-butyl or tert.-butyl group.

If an amino group is substituted by 2 alkyl residues, these residues can also be closed to form a ring in such a way that as a whole they represent a ring interrupted by a nitrogen atom. In this connection those amino groups are preferred which represent an overall 5- or 6-membered ring and which in turn is optionally interrupted by oxygen, sulphur or nitrogen. The morpholino residue is particularly preferred.

"Alkoxy"—also as in alkoxy and aralkoxycarbonyl residues—represents a straight-chained or branched alkoxy residue with 1–6, preferably 1–4 C atoms. Examples are the methoxy, ethoxy, propyloxy, iso-butyloxy or tert.-butyloxy group.

"Aryl"—also as in arylcarbamoyl groups—denotes a carbon aromatic or heteroaromatic residue, preferably one with 6–10 ring atoms in particular a phenyl or naphthyl group which can additionally be substituted by alkyl, alkoxy or/and halogen. A phenyl residue is particularly preferred.

An "aralkyl" residue—also as in an aralkylcarbamoyl group—denotes a residue in which an alkyl group defined as above is substituted by an aryl residue characterized as above. A benzyl group is preferred.

An "aralkoxy" residue for example in aralkoxycarbonyl groups denotes a residue in which an alkoxy group as defined above is substituted by an aryl residue as defined above. A benzyloxy group is preferred.

"Halogen" represents the residues fluorine, chlorine, bromine and iodine. Fluorine and chlorine are preferred.

An acyl group denotes a carboxylic acid residue which can contain alkyl, aralkyl or aryl residues. Acetyl, phenylacetyl or benzoyl residues are preferred.

An alkylene group is a straight-chained or branched, saturated or unsaturated hydrocarbon chain comprising 3–5, preferably 3 or 4 C atoms, with two free binding sites.

Examples are —CH$_2$—CH=CH—,

—CH=C—CH$_2$—, —CH—CH=CH—,
      |             |
      CH$_3$       CH$_3$

—(CH$_2$)$_4$— or —CH=CH—CH=CH—.

A butadiendiyl residue (—CH=CH—CH=CH—) and a tetramethylene residue (—(CH$_2$)$_4$—) are preferred.

An alkenyl residue is a straight-chained or branched carbon residue of 2–5 C atoms with at least one double bond. A vinyl residue is for example preferred. A dialkylphosphinyl group is understood as the residue

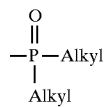

in which alkyl has the meaning given above. A dimethylphosphinyl residue is preferred.

Alkali or alkaline earth or ammonium salts can be used as salts of SO$_3$H, PO$_3$H$_2$ and carboxy residues. Alkali salts are understood as lithium, sodium, potassium, rubidium and caesium salts, of which lithium, sodium and potassium salts and above all sodium and potassium salts are preferred. Alkaline earth salts are those of beryllium, magnesium, calcium, strontium or barium. Magnesium and calcium salts are preferred and calcium salts are particularly preferred. Salts of the unsubstituted ammonium ion NH$_4^+$ can be used as ammonium salt. It is, however, also possible to use those ammonium salts in which the ammonium ion is substituted by 1–4 alkyl, aryl or aralkyl residues. The definitions given above apply to these residues in which methyl, ethyl and n-propyl are particularly preferred as the alkyl residue, a phenyl group as the aryl residue and a benzyl group as the aralkyl residue.

A carboxamido residue is understood as the residue CONH$_2$ and also those residues in which the amino group is substituted by one or two alkyl residues which optionally carry one or several hydroxy, carboxy or/and alkoxycarbonyl residues.

Those compounds are preferred among the nitroso compounds of the general formula II used according to the invention in which R[7] and R[8] form a saturated or unsaturated chain as described above. In this connection it is particularly preferred when this chain is unsaturated and free nitrogen electron pairs of the unsaturated chain are in conjugation with the double bond and with the bridge N atom of the general formula II so that an anellated aromatic ring results.

Tautomeric forms may also be possible for a substance of the general formula II. These should also be considered to be encompassed by the general formula II.

Nitroso compounds of the general formulae III to XII are preferred according to the invention.

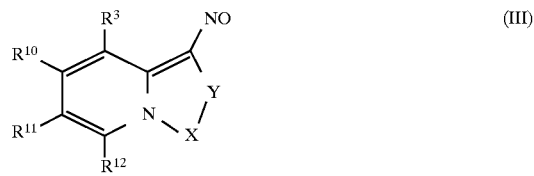

(III)

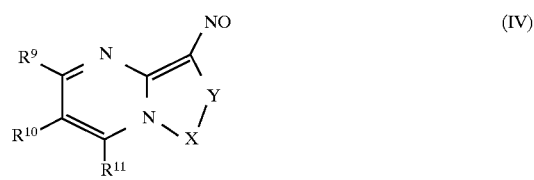

(IV)

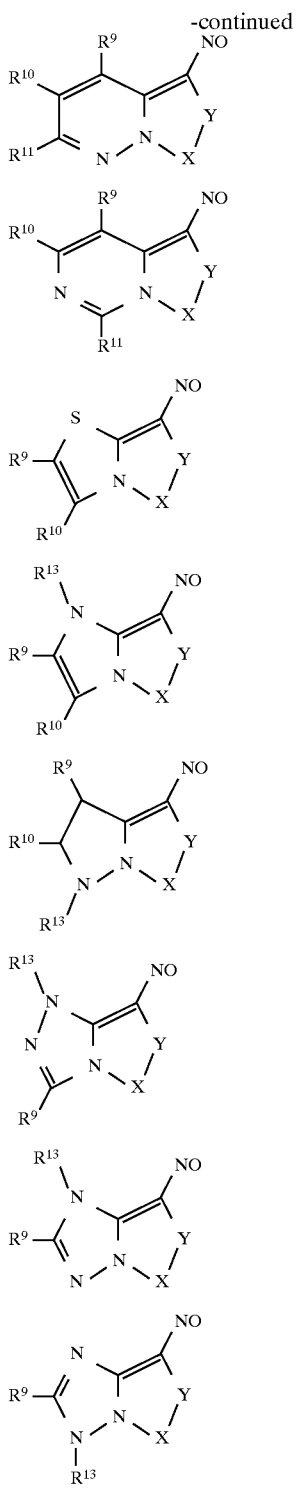

as well as corresponding tautomeric forms and salts thereof.

In this connection X—Y has the same meaning as described above. $R^9$, $R^{10}$, $R^{11}$ and $R^{12}$ which are the same or different represent hydrogen, hydroxy, alkyl, alkoxy, alkylthio, aralkyl, aryl, carboxy, alkoxycarbonyl, carboxamido, cyano, amino which optionally is substituted by one or two alkyl residues optionally carrying one or several hydroxy, carboxy or/and alkoxycarbonyl residues or they represent halogen in which two neighbouring residues optionally form an alkylene group which in turn is optionally substituted with aryl or is anellated and $R^{13}$ represents alkyl or aralkyl which can optionally be substituted by hydroxy, carboxy, $SO_3H$, $PO_3H_2$ or dialkylphosphinyl. The definitions of the residues correspond to those stated for the substances of the general formula II.

Substances of the general formulae III, IV, V, VII, VIII and IX, if desired corresponding tautomeric forms and salts thereof are particularly preferred for the use according to the invention. Those substances are particularly preferred in which X—Y has the meaning $N=CR^6$ in which $R^6$ can have the meaning which is stated for the general formula II.

The compounds 3-nitroso-2-methyl-pyrazolo-[1.5a]-pyridine, 3-nitroso-pyrazolo-[1.5a]-pyridine and 3-nitroso-pyrazolo [3.2-c]-s-triazole and salts thereof, in particular hydrochloride, have in particular proven to be excellently suitable for the use according to the invention.

Substituted aromatic compounds, in particular phenols and naphthols with a readily substitutable group, are preferably used as the coupler substance BX. Halogens and in particular bromine and chlorine or a $SO_3H$ group are preferably used as the substitutable cleavable group.

The preferred reaction principle according to the invention is thus a nucleophilic aromatic substitution of the cleavable group X of the compound BX by the reduced compound A'.

Preferred compounds BX are 2,4,6-trihalogen-3-hydroxybenzoic acid, 2,4-dihalogen-1-naphthol, 1-naphthol-4-sulfonic acid, 4-monohalogen-anilines, 4-monohalogenphenols and 4-monohalogen-naphthols.

Depending on the nature of the cleaved group $X^-$, the concentration of this group can be measured amperometrically or potentiometrically. If the cleaved group is a halogenide ion, then it is preferable to measure potentiometrically against an Ag/Ag halogenide electrode or calomel electrode. Other cleavable groups such as the $SO_3^-$ group can also be measured amperometrically by oxidation on the electrode.

The colour formed of the coupling product A'B is also measured colorimetrically at the same time as the electrochemical measurement of the cleaved group $X^-$. This can be achieved visually or preferably by means of a photometer. In this process the colorimetric and potentiometric measurements complement each other in an ideal manner since the colorimetric measurement is advantageous in particular at low concentrations whereas the electrochemical measurement enables a more accurate determination at higher concentrations. Moreover the colour formation can be used to monitor the functioning of the electrochemical detection system.

For a direct amperometric measurement the reaction mixture is in contact with an inert solid electrode (e.g. a platinum electrode) which is capable of accepting electrons from the cleavable group and which forms one electrode of a half cell. The half cell is conductively connected to a second electrode on which a reducing reaction can take place (e.g. a silver/silver chloride electrode, calomel electrode or platinum/ferrocyanide). A salt bridge preferably forms a liquid connection between the two electrodes.

For the potentiometric measurement of the cleaved off ions $X^-$ it is advantageous to use ion-sensitive electrodes such as for example chloride- or bromide-sensitive electrodes. A wide range of these is commercially available. Suitable electrode arrangements and measuring procedures are known to a person skilled in the art.

The method according to the invention is preferably carried out in an aqueous, non-electrochemically active solution. An agent according to the invention preferably contains a buffer system in order to maintain a suitable pH value for carrying out the method which depends especially on the enzyme used. The buffer system of the test solution advantageously sets a pH value between 4 and 9, in particular between 5 and 7.

The agent according to the invention can be present in the form of a solution or be present in a dry form after having applied the solution to an absorptive or swellable carrier and then having dried this carrier. When in the form of a solution, the agent preferably contains all reagents required for the method. Water as well as mixtures with water-soluble organic solvents such as for example methanol, ethanol, acetone or dimethylformamide preferably come into consideration as solvents. For reasons of stability it may be advantageous to divide the reagents required for the test into two or several solutions, which are not mixed until the actual assay. The concentration of the artificial electron acceptor used depends on the concentration of the analyte to be measured.

Typical concentrations of the analytes to be measured by the method according to the invention are $10^{-6}$ to $10^{-2}$ mol/l in particular $10^{-5}$ to $10^{-2}$ mol/l. Correspondingly typical concentrations of the artificial electron acceptors A used are $10^{-4}$ to $10^{-1}$ mol/l. The concentration of the oxidizing enzyme depends on its activity and the concentration of the analyte. Typical values for enzyme concentrations are 1 mU/ml to 1 U/ml in the case of cuvette tests.

The compound BX capable of coupling is used in at least a stoichiometric ratio to compound A, preferably in a 1.5- to 2-fold excess.

The agent according to the invention can also be present in the form of a test strip. Various embodiments are known for such test strips. In a test strip the reagents required for carrying out the method of determination are present on solid carrier layers. Absorptive and/or swellable materials come into particular consideration as carrier layers which are wetted by the sample liquid to be examined. The reagents are present in a solid form in or on the carrier material. When the sample liquid is applied to the test strip or the test strip is immersed in the sample liquid a liquid environment forms in the strip within which the detection reaction takes its course. The electrode needed to measure the cleavable group $X^-$ is in this case in a liquid conductive contact with the liquid environment of the reaction mixture.

The preferred concentrations of the individual reagents on the test strips are:

analyte typically $10^{-4}$ to $10^{-1}$M chromogen A $10^{-3}$ to 1M substance BX capable of coupling $10^{-3}$ to 1M enzyme 0.1 to 100 U per test zone

EXAMPLE 1

Glucose detection by means of colour formation and electrochemical detection
Reaction equation

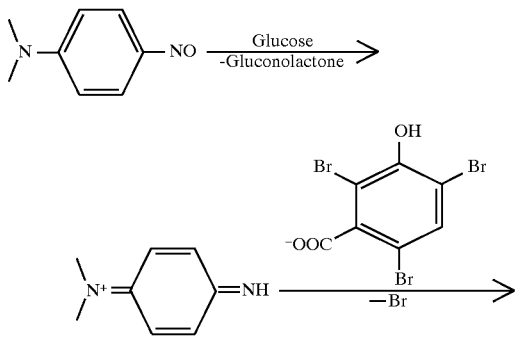

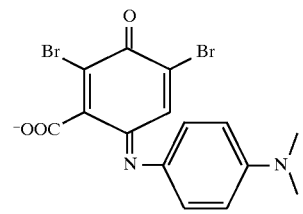

Measuring mixture (final concentration)

100 mM citrate buffer pH 5.8
10 mM 2,4,6-tribromo-3-hydroxybenzoic acid
1 mM N,N-bis-(2-hydroxyethyl)-4-nitrosoaniline
10 U/ml glucose-dye-oxidoreductase (PQQ-dependent glucose dehydrogenase)
0.1M sodium nitrate glucose is added as the analyte at various concentrations between 100 and 500 $\mu$M.

Measurement a) Electrochemical measurement

The bromide ions that are released during the reductive coupling of the quinonediimine A' with 2,4,6-tribromo-3-hydroxybenzoic acid are measured by means of an ion-sensitive electrode from the Ingold Company, Type 373-90-WTE-ISE-S7 in conjunction with a minivolt meter from the Knick Company (Type 763). The result is shown in FIG. 1.

b) Colorimetric measurement

Figure 2:
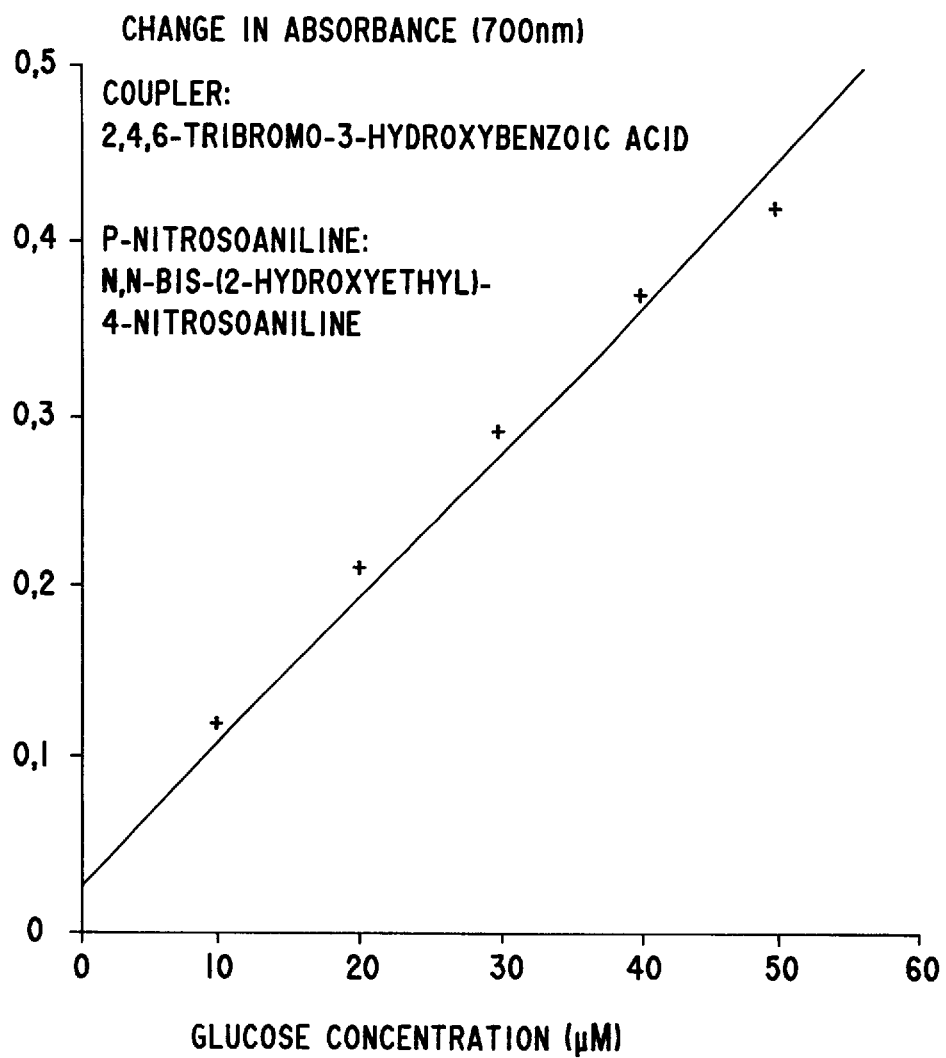
FIG. 2: Glucose-dependent reductive coupling with release of bromide ions. Change in absorbance (700 nm).

In parallel to the increase of the bromide concentration (decrease in the measuring chain voltage of the bromide-sensitive electrode) with increasing glucose concentration, the increasing formation of a green dye A'B with $\lambda$max.=705 nm is observed (FIG. 2).

We claim:

1. A method for the simultaneous colorimetric and electrochemical measurement of an analyte, comprising:

(a) reducing a chromogen A to a compound A' by reacting the analyte with an oxidizing enzyme to oxidize the analyte and transferring electrons produced thereby onto the chromogen A, (b) reacting the compound A' with a substance BX to form a colored substance A'B and an electrochemically measurable group $X^-$, (c) colorimetrically measuring or detecting the colored substance A'B as an indication of amount or presence, respectively, of the analyte, and (d) electrochemically measuring the electrochemically measurable group $X^-$ as an indication of amount of the analyte.

2. The method of claim 1, wherein in the reducing step (a), the electrons are transferred onto the chromogen A via a mediator.

3. The method of claim 2, wherein the mediator comprises phenazine methosulfate or diaphorase.

4. The method of claim 1, wherein the oxidizing enzyme comprises a dehydrogenase.

5. The method of claim 1, wherein the chromogen A comprises an aromatic nitroso compound.

6. The method of claim 5, wherein the aromatic nitroso compound comprises a compound of formula I

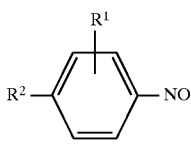

(I)

wherein
- R¹ is selected from the group consisting of hydrogen; hydroxy; alkyl which is unsubstituted or has a substituent selected from the group consisting of (a) hydroxy, (b) COOH, (c) $PO_3H_2$ and (d) $SO_3H$; alkoxy; alkylthio; aryloxy; arylthio; halogen; and amino which is unsubstituted or has at least one alkyl substituent, which at least one alkyl substituent is unsubstituted or has a substituent selected from the group consisting of (a) hydroxy, (b) $PO_3H_2$, (c) dialkyl-phosphinyl, (d) $SO_3H$ and (e) $CO_2H$;
- R² is selected from the group consisting of hydroxy; alkoxy; aryloxy; arylthio; alkylthio; and amino group $NR^3R^4$,
  - wherein the alkyl residue of the alkoxy or alkylthio is unsubstituted or has a substituent selected from the group consisting of (a) hydroxy, (b) alkoxy and (c) amino which is unsubstituted or has at least one substituent selected from the group consisting of (1) alkyl, (2) $PO_3H_2$, or a salt thereof, (3) $SO_3H$, or a salt thereof, and (4) $CO_2H$, or a salt thereof, and
  - wherein R³ and R⁴ are the same or different, and each is independently selected from the group consisting of (a) hydrogen, (b) aryl and (c) alkyl, wherein each of (b) aryl or (c) alkyl is unsubstituted or has a substituent selected from the group consisting of (1) hydroxy, (2) alkoxy, (3) hydroxyalkoxy, (4) polyalkoxy which is unsubstituted or substituted by hydroxy, (5) $PO_3H_2$, or a salt thereof, (6) $SO_3H$, or a salt thereof, (7) COOH, or a salt thereof, and (8) an amino group which is unsubstituted or substituted at least once by alkyl, or
    - wherein R³ and R⁴ together are an alkylene residue which is uninterrupted or interrupted by oxygen, sulphur or nitrogen, wherein the nitrogen is substituted by a substituent selected from the group consisting of alkyl, hydroxyalkyl, hydroxyalkoxyalkyl, alkoxyhydroxyalkyl, alkoxycarbonylalkyl, dioxanylylalkyl and polyalkoxyalkyl, wherein each substituent of the nitrogen is unsubstituted or substituted in the alkyl moiety by a hydroxy residue, or
    - if R¹ is in the ortho position relative to $NR^3R^4$, one of R³ and R⁴ is additionally selected from an alkylene residue together with R¹.

7. The method of claim 6, wherein R¹ is hydrogen or $C_1$–$C_6$ alkyl.

8. The method of claim 6, wherein R is $C_1$–$C_6$ alkoxy or amino group $NR^3R^4$.

9. The method of claim 6, wherein the compound is selected from the group consisting of
  N,N'-bis-(2-hydroxyethyl)-p-nitrosoaniline
  N,N'-dimethyl-p-nitrosoaniline
  N,N'-diethyl-p-nitrosoaniline
  N-methyl-N'-(4-nitrosophenyl)-piperazine
  N-(2-hydroxyethyl)-5-nitrosoindoline
  2,4-dimethoxy-nitrosobenzene
  N,N'-bis-(2-methoxyethyl)-4-nitrosoaniline
  N-(4-nitrosophenyl)-morpholine
  N-(2,2-diethoxy-ethyl)N'-(4-nitrosophenyl)-piperazine
  p-nitrosophenol
  3-methoxy-4-nitrosophenol.

10. The method of claim 5, wherein the aromatic nitroso compound comprises a compound of formula II

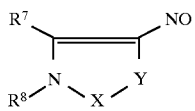

(II)

wherein
- X—Y is $NR^5$—CO or N=$CR^6$
- R⁵ is selected from the group consisting of (a) hydrogen, (b) alkyl, which is unsubstituted or has a substituent selected from the group consisting of (1) hydroxy, (2) carboxy, (3) $SO_3H_2$, (4) $PO_3H_2$ and (5) dialkylphosphinyl,
- $R_6$ is selected from the group consisting of (a) hydrogen, (b) alkyl, (c) alkenyl, (d) alkoxy, (e) alkylthio, (f) aryl, (g) arylthio, (h) aralkyl, wherein each of (b)–(h) is unsubstituted or has a substituent selected from the group consisting of (1) hydroxy, (2) carboxy, or a salt thereof, (3) $SO_3H$, or a salt thereof, (4) $PO_3H_2$, or a salt thereof, and (5) alkoxycarbonyl,
  - (i) carboxy, (j) alkoxycarbonyl, (k) carboxyamido, (l) halogen, (m) amino which is unsubstituted or substituted by one or two alkyl residues which are unsubstituted or substituted by at least one residue selected from the group consisting of hydroxy, carboxy, and alkoxycarbonyl, wherein when amino is substituted by two alkyl residues, the two alkyl residues are unclosed or closed to from a ring that, in addition to the N atom of the amino group, is uninterrupted or interrupted by oxygen, sulphur or a further nitrogen atom, and (n) amino which is unsubstituted or substituted by up to two substituents, each independently selected from the group consisting of acyl, alkoxy, aralkoxycarbonyl, $H_2N$—CO, alkyl, aralkyl and arylcarbamoyl,
- R⁷ is selected from the group consisting of (a) alkyl, (b) thioalkyl, (c) aralkyl, wherein each of (a)–(c) is unsubstituted or has a substituent selected from the group consisting of (1) hydroxy, (2) carboxy, (3) $SO_3H$ and (4) $PO_3H_2$, and (d) amino which is unsubstituted or substituted by one or two alkyl groups, which alkyl groups are unsubstituted or have a substituent selected from the group consisting of (1) hydroxy, (2) carboxy, (3) $SO_3H$, (4) dialkylphosphinyl and (5) $PO_3H_2$,
- wherein at least one of R⁶ and R⁷ are an amino group and R⁸ is alkyl or aralkyl, wherein R⁸ is unsubstituted or has a substituent selected from the group consisting of hydroxy, carboxy, $SO_3H$ and $PO_3H_2$, or
- R⁷ and R⁸ together are a saturated or unsaturated chain having 3 or 4 members of nitrogen atoms or of carbon atoms, which saturated or unsaturated chain further contains zero or at least one nitrogen or sulphur atom, wherein the carbon atoms are unsubstituted or have a substituent selected from the group consisting of alkyl, alkoxy, alkylthio, hydroxy, aralkyl, aryl, carboxy, carboxamido, alkoxycarbonyl, cyano, halogen and amino, which amino is unsubstituted or substituted by one or two alkyl residues which are each unsubstituted or substituted by one or more substituents selected from the group consisting of (a) hydroxy, (b) carboxy, and (c) alkoxycarbonyl, wherein nitrogen atoms that are not bound via a double bond are substituted by alkyl or aralkyl, which alkyl or aralkyl are each independently unsubstituted or have a substituent selected from the group consisting of hydroxy, SO$_3$H, PO$_3$H$_2$, carboxy and dialkylphosphinyl, or two neighboring chain substituents form an alkylene group which is unsubstituted or substituted with aryl or is anellated, a tautomeric form or a salt thereof.

11. The method of claim 10, wherein the aromatic nitroso compound comprises a compound selected from the group consisting of formulae III to XII

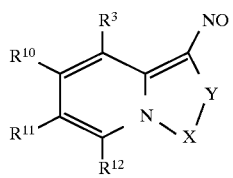
(III)

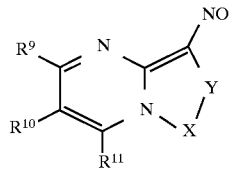
(IV)

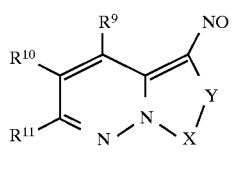
(V)

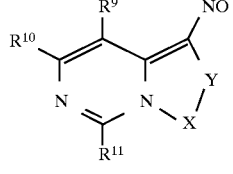
(VI)

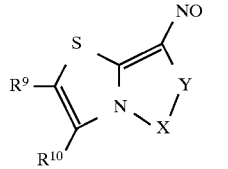
(VII)

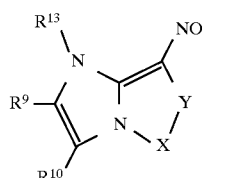
(VIII)

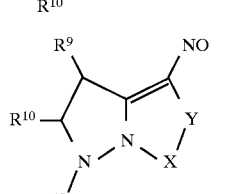
(IX)

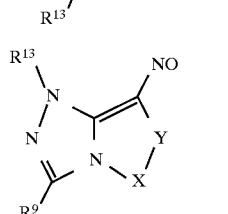
(X)

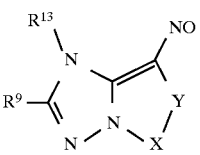
(XI)

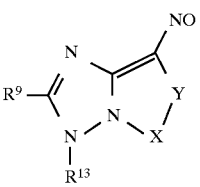
(XII)

wherein

R$^9$, R$^{10}$, R$^{11}$ and R$^{12}$ are the same or different and each independently is selected from the group consisting of hydrogen, hydroxy, halogen, alkyl, akloxy, aklylthio, aralkyl, aryl, carboxy, alkoxycarbonyl, carboxamido, cyano, amino which is unsubstituted or substituted by one or two alkyl residues each of which is unsubstituted or substituted by at least one substituent selected from the group consisting of hydroxy, carboxy and alkoxycarbonyl, wherein two neighboring residues form an alkylene group which is unsubstituted or substituted by aryl or is anellated, and R$^{13}$ is alkyl or aralkyl, each of which is unsubstituted or substituted by a substituent selected from the group consisting of hydroxy, carboxy, SO$_3$H, PO$_3$H$_2$ and dialkylphosphinyl.

12. The method of claim 11, wherein the aromatic nitroso compound comprises a compound selected from the group consisting of formulae III, IV, V, VII, VIII and IX.

13. The method of claim 11, wherein X—Y is N=CR$^6$.

14. The method of claim 5, wherein the aromatic nitroso compound is selected from the group consisting of
3-nitroso-2-methyl-pyrazolo-[1.5a]-pyridine,
3-nitroso-pyrazolo-[1.5a]-pyridine and
3-nitroso-pyrazolo [3.2-c]-s-triazole,
or a salt thereof.

15. The method of claim 1, wherein in the substance BX, B comprises an aromatic compound and X comprises a substituent which is substituted or unsubstituted.

16. The method of claim 15, wherein B comprises phenol or naphthol.

17. The method of claim 15, wherein X comprises halogen or SO$_3$H.

18. The method of claim 1, wherein BX comprises aniline or naphthylamine.

19. The method of claim 1, wherein BX comprises 2,4,6-trihalogen-3-hydroxy-benzoic acid, 2,4-dihalogen-1-naphthol, 1-naphthol-4-sulfonic acid, 4-monohalogen-aniline, 4-monohalogen-phenol and 4-monohalogen-naphthol.

20. The method of claim 1, wherein the electrochemically measurable group X$^-$ is measured potentiometrically.

21. The method of claim 1, wherein the electrochemically measurable group X$^-$ is measured amperometrically.

22. The method of claim 1, wherein the analyte is present in a concentration of $10^{-6}$ to $10^{-2}$ mol/l.

23. The method of claim 1, wherein the chromogen A is present in a concentration of $10^{-4}$ to $10^{-1}$ mol/l.

24. The method of claim 1, wherein the oxidizing enzyme is present in a concentration of 1 mU/ml to 1 U/ml.

25. The method of claim 1, wherein the substance BX is present in from a stoichiometric ratio to a 2-fold excess, compared to the chromogen A.

26. A kit for the simultaneous colorimetric and electrochemical measurement of an analyte, comprising:
  (a) a set of reagents, comprising
    (1) an oxidizing enzyme which oxidizes the analyte,
    (2) a chromogen A which accepts electrons produced in an oxidation reaction of the oxidizing enzyme and the analyte to produce a compound A', and
    (3) a substance BX which reacts with the compound A' to form a colored substance A'B and an electrochemically measurable group X$^-$; and
  (b) a sensor electrode for electrochemically measuring the electrochemically measurable group X$^-$.

27. The kit of claim 26, wherein each of the set of reagents is separately packaged.

28. The kit of claim 26, wherein the set of reagents are packaged together.

29. The kit of claim 28, further comprising an aqueous solution, wherein the aqueous solution contains the set of reagents, the aqueous solution comprising a buffer which sets a pH value of between 4 and 9 in the aqueous solution.

30. The kit of claim 26, further comprising an optical measuring device for colorimetrically measuring or detecting the colored substance A'B.

31. The kit of claim 26, further comprising a mediator which transfers electrons produced in the oxidation reaction of the oxidizing enzyme and the analyte to the chromogen A.

32. The kit of claim 31, wherein the mediator comprises phenazine methosulfate or diaphorase.

33. The kit of claim 26, wherein the oxidizing enzyme comprises a dehydrogenase.

34. The kit of claim 26, wherein the chromogen A comprises an aromatic nitroso compound.

35. The kit of claim 34, wherein the aromatic nitroso compound comprises a compound of formula I

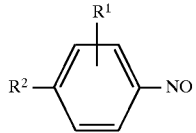

(I)

wherein
  $R^1$ is selected from the group consisting of hydrogen; hydroxy; alkyl which is unsubstituted or has a substituent selected from the group consisting of (a) hydroxy, (b) COOH, (c) PO$_3$H$_2$ and (d) SO$_3$H; alkoxy; alkylthio; aryloxy; arylthio; halogen; and amino which is unsubstituted or has at least one alkyl substituent, which at least one alkyl substituent is unsubstituted or has a substituent selected from the group consisting of (a) hydroxy, (b) PO$_3$H$_2$, (c) dialkyl-phosphinyl, (d) SO$_3$H and (e) CO$_2$H;
  $R^2$ is selected from the group consisting of hydroxy; alkoxy; aryloxy; arylthio; alkylthio; and amino group NR$^3$R$^4$,
    wherein the alkyl residue of the alkoxy or alkylthio is unsubstituted or has a substituent selected from the group consisting of (a) hydroxy, (b) alkoxy and (c) amino which is unsubstituted or has at least one substituent selected from the group consisting of (1) alkyl, (2) PO$_3$H$_2$, or a salt thereof, (3) SO$_3$H, or a salt thereof, and (4) CO$_2$H, or a salt thereof, and
    wherein R$^3$ and R$^4$ are the same or different, and each is independently selected from the group consisting of (a) hydrogen, (b) aryl and (c) alkyl, wherein each of (b) aryl or (c) alkyl is unsubstituted or has a substituent selected from a group consisting of (1) hydroxy, consisting of (1) hydroxy, (2) alkoxy, (3) hydroxyalkoxy, (4) polyalkoxy which is unsubstituted or substituted by hydroxy, (5) PO$_3$H$_2$, or a salt thereof, (6) SO$_3$H, or a salt thereof, (7) COOH, or a salt thereof, and (8) an amino group which is unsubstituted or substituted at least once by alkyl, or
  wherein R$^3$ and R$^4$ together are an alkylene residue which is uninterrupted or interrupted by oxygen, sulphur or nitrogen, wherein the nitrogen is substituted by a substituent selected from the group consisting of alkyl, hydroxyalkyl, hydroxyalkoxyalkyl, alkoxyhydroxyalkyl, alkoxycarbonylalkyl, dioxanylylalkyl and polyalkoxyalkyl, wherein each substituent of the nitrogen is unsubstituted or substituted in the alkyl moiety by a hydroxy residue, or
  if R$^1$ is in the ortho position relative to NR$^3$R$^4$, one of R$^3$ and R$^4$ is additionally selected from an alkylene residue together with R$^1$.

36. The kit of claim 35, wherein R$^1$ is hydrogen or C$_1$–C$_6$ alkyl.

37. The kit of claim 35, wherein R$^2$ is C$_1$–C$_6$ alkoxy or amino group NR$^3$R$^4$.

38. The kit of claim 35, wherein the compound is selected from the group consisting of
  N,N'-bis-(2-hydroxyethyl)-p-nitrosoaniline
  N,N'-dimethyl-p-nitrosoaniline
  N,N'-diethyl-p-nitrosoaniline
  N-methyl-N'-(4-nitrosophenyl)-piperazine
  N-(2-hydroxyethyl)-5-nitrosoindoline
  2,4-dimethoxy-nitrosobenzene
  N,N'-bis-(2-methoxyethyl)-4-nitrosoaniline
  N-(4-nitrosophenyl)-morpholine
  N-(2,2-diethoxy-ethyl)N'-(4-nitrosophenyl)-piperazine
  p-nitrosophenol
  3-methoxy-4-nitrosophenol.

39. The kit of claim 34, wherein the aromatic nitroso compound comprises a compound of formula II

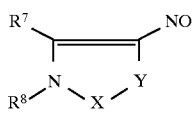

(II)

wherein
  X—Y is NR$^5$—CO or N=CR$^6$
  R$^5$ is selected from the group consisting of (a) hydrogen, (b) alkyl, which is unsubstituted or has a substituent selected from the group consisting of (1) hydroxy, (2) carboxy, (3) SO$_3$H, (4) PO$_3$H$_2$ and (5) dialkylphosphinyl,
  R$_6$ is selected from the group consisting of (a) hydrogen, (b) alkyl, (c) alkenyl, (d) alkoxy, (e) alkylthio, (f) aryl, (g) arylthio, (h) aralkyl, wherein each of (b)–(h) is unsubstituted or has a substituent selected from the group consisting of (1) hydroxy, (2) carboxy, or a salt thereof, (3) SO$_3$H or a salt thereof, (4) PO$_3$H$_2$, or a salt thereof, and (5) alkoxycarbonyl,
    (i) carboxy, (j) alkoxycarbonyl, (k) carboxyamido, (l) halogen, (m) amino which is unsubstituted or substituted by one or two alkyl residues which are unsubstituted or substituted by at least one residue selected from the group consisting of hydroxy, carboxy, and alkoxycarbonyl, wherein when amino is substituted by two alkyl residues, the two alkyl residues may additionally be closed to from a ring that, in addition to the N atom of the amino group, is uninterrupted or interrupted by oxygen, sulphur or a further nitrogen atom, and (n) amino which is unsubstituted or substituted by up to two substituents, each independently selected from the group consisting of acyl, alkoxy, aralkoxycarbonyl, $H_2N$—CO, alkyl, aralkyl and arylcarbamoyl, $R^7$ is selected from the group consisting of (a) alkyl, (b) thioalkyl, (c) aralkyl, wherein each of (a)–(c) is unsubstituted or has a substituent selected from the group consisting of (1) hydroxy, (2) carboxy, (3) $SO_3H$ and (4) $PO_3H_2$, and (d) amino which is unsubstituted or substituted by one or two alkyl groups, which alkyl groups are unsubstituted or have a substituent selected from the group consisting of (1) hydroxy, (2) carboxy, (3) $SO_3H$, (4) dialkylphosphinyl and (5) $PO_3H_2$, wherein at least one of $R^6$ and $R^7$ are an amino group and $R^8$ is alkyl or aralkyl, wherein $R^8$ is unsubstituted or has a substituent selected from the group consisting of hydroxy, carboxy, $SO_3H$ and $PO_3H_2$, $R^7$ and $R^8$ together are a saturated or unsaturated chain having 3 or 4 members of nitrogen atoms or of carbon atoms, which saturated or unsaturated chain further contains zero or at least one nitrogen or sulphur atom, wherein the carbon atoms are unsubstituted or have a substituent selected from the group consisting of alkyl, alkoxy, alkylthio, hydroxy, aralkyl, aryl, carboxy, carboxamido, alkoxycarbonyl, cyano, halogen and amino, which amino is unsubstituted or substituted by one or two alkyl residues which are each unsubstituted or substituted by one or more substituents selected from the group consisting of (a) hydroxy, (b) carboxy, and (c) alkoxycarbonyl, wherein nitrogen atoms that are not bound via a double bond are substituted by alkyl or aralkyl, which alkyl or aralkyl are each independently unsubstituted or have a substituent selected from the group consisting of hydroxy, $SO_3H$, $PO_3H_2$, carboxy and dialkylphosphinyl, or two neighboring chain substituents may additionally form an alkylene group which is unsubstituted or substituted with aryl or is anellated, a tautomeric form or a salt thereof.

40. The kit of claim 39, wherein the aromatic nitroso compound comprises a compound selected from the group consisting of formulae III to XII

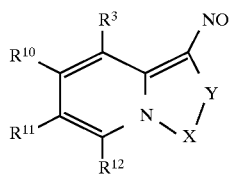

(III)

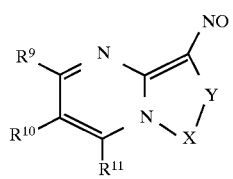

(IV)

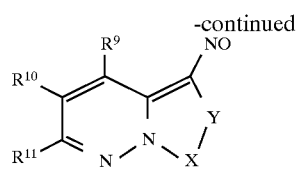

(V)

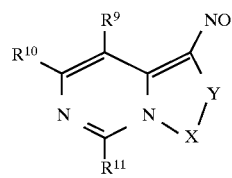

(VI)

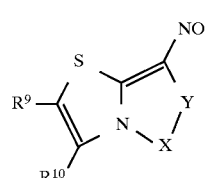

(VII)

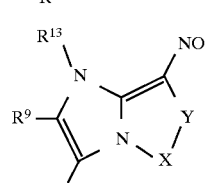

(VIII)

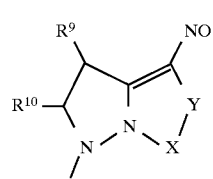

(IX)

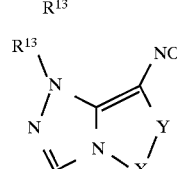

(X)

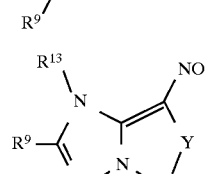

(XI)

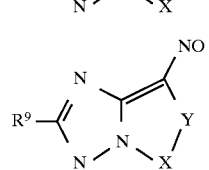

(XII)

wherein $R^9$, $R^{10}$, $R^{11}$ and $R^{12}$ are the same or different and each independently is selected from the group consisting of hydrogen, hydroxy, halogen, alkyl, akloxy, aklylthio, aralkyl, aryl, carboxy, alkoxycarbonyl, carboxamido, cyano, amino which is unsubstituted or substituted by one or two alkyl residues each of which is unsubstituted or substituted by at least one substituent selected from the group consisting of hydroxy, carboxy and alkoxycarbonyl, wherein two neighboring residues can additionally form an alkylene group which is unsubstituted or substituted by aryl or is anellated, and $R^{13}$ is alkyl or aralkyl, each of which is unsubstituted or substituted by a substituent selected from the group consisting of hydroxy, carboxy, $SO_3H$, $PO_3H_2$ and dialkylphosphinyl.

41. The kit of claim 40, wherein the aromatic nitroso compound comprises a compound selected from the group consisting of formulae III, IV, V, VII, VIII and IX.

42. The kit of claim 40, wherein X—Y is $N=CR^6$.

43. The kit of claim 35, wherein the aromatic nitroso compound is selected from the group consisting of 3-nitroso-2-methyl-pyrazolo-[1.5a]-pyridine, 3-nitroso-pyrazolo-[1.5a]-pyridine and 3-nitroso-pyrazolo [3.2-c]-s-triazole, or a salt thereof.

44. The kit of claim 26, wherein in the substance BX, B comprises an aromatic compound and X comprises a substituent which is substituted or unsubstituted.

45. The kit of claim 44, wherein B comprises phenol or naphthol.

46. The kit of claim 44, wherein X comprises halogen or $SO_3H$.

47. The kit of claim 26, wherein BX comprises aniline or naphthylamine.

48. The kit of claim 26, wherein BX comprises 2,4,6-trihalogen-3-hydroxy-benzoic acid, 2,4-dihalogen-1-naphthol, 1-naphthol-4-sulfonic acid, 4-monohalogen-aniline, 4-monohalogen-phenol and 4-monohalogen-naphthol.

49. The kit of claim 26, wherein the chromogen A is present in a concentration of $10^{-4}$ to $10^{-1}$ mol/l.

50. The kit of claim 26, wherein the oxidizing enzyme is present in a concentration of 1 mU/ml to 1 U/ml.

51. The kit of claim 26, wherein the substance BX is present in from a stoichiometric ratio to a 2-fold excess, compared to the chromogen A.

52. A test element for the simultaneous colorimetric and electrochemical measurement of an analyte, comprising a set of reagents, present in or on at least one solid carrier, the set of reagents comprising:

(a) an oxidizing enzyme which oxidizes the analyte;

(b) a chromogen A which accepts electrons produced in an oxidation reaction of the oxidizing enzyme and the analyte to produce a compound A'; and (c) a substance BX which reacts with the compound A' to form a colored substance A'B and an electrochemically measurable group $X^-$.

53. The test element of claim 52, further comprising a mediator which transfers electrons produced in the oxidation reaction of the oxidizing enzyme and the analyte to the chromogen A.

54. The test element of claim 53, wherein the mediator comprises phenazine methosulfate or diaphorase.

55. The test element of claim 52, wherein the oxidizing enzyme comprises a dehydrogenase.

56. The test element of claim 52, wherein the chromogen A comprises an aromatic nitroso compound.

57. The test element of claim 56, wherein the aromatic nitroso compound comprises a compound of formula I

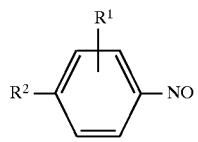

wherein $R^1$ is selected from the group consisting of hydrogen; hydroxy; alkyl which is unsubstituted or has a substituent selected from the group consisting of (a) hydroxy, (b) COOH, (c) $PO_3H_2$ and (d) $SO_3H$; alkoxy; alkylthio; aryloxy; arylthio; halogen; and amino which is unsubstituted or has at least one alkyl substituent, which at least one alkyl substituent is unsubstituted or has a substituent selected from the group consisting of (a) hydroxy, (b) $PO_3H_2$, (c) dialkyl-phosphinyl, (d) $SO_3H$ and (e) $CO_2H$;

$R^2$ is selected from the group consisting of hydroxy; alkoxy; aryloxy; arylthio; alkylthio; and amino group $NR^3R^4$, wherein the alkyl residue of the alkoxy or alkylthio is unsubstituted or has a substituent selected from the group consisting of (a) hydroxy, (b) alkoxy and (c) amino which is unsubstituted or has at least one substituent selected from the group consisting of (1) alkyl, (2) $PO_3H_2$, or a salt thereof, (3) $SO_3H$, or a salt thereof, and (4) $CO_2H$, or a salt thereof, and wherein $R^3$ and $R^4$ are the same or different, and each is independently selected from the group consisting of (a) hydrogen, (b) aryl and (c) alkyl, wherein each of (b) aryl or (c) alkyl is unsubstituted or has a substituent selected from the group consisting of (1) hydroxy, (2) alkoxy, (3) hydroxyalkoxy, (4) polyalkoxy which is unsubstituted or substituted by hydroxy, (5) $PO_3H_2$, or a salt thereof, (6) $SO_3H$, or a salt thereof, (7) COOH, or a salt thereof, and (8) an amino group which is unsubstituted or substituted at least once by alkyl, or wherein $R^3$ and $R^4$ together are an alkylene residue which is uninterrupted or interrupted by oxygen, sulphur or nitrogen, wherein the nitrogen is substituted by a substituent selected from the group consisting of alkyl, hydroxyalkyl, hydroxyalkoxyalkyl, alkoxyhydroxyalkyl, alkoxycarbonylalkyl, dioxanylylalkyl and polyalkoxyalkyl, wherein each substituent of the nitrogen is unsubstituted or substituted in the alkyl moiety by a hydroxy residue, or if $R^1$ is in the ortho position relative to $NR^3R^4$, one of $R^3$ and $R^4$ is additionally selected from an alkylene residue together with $R^1$.

58. The test element of claim 57, wherein $R^1$ is hydrogen or $C_1$–$C_6$ alkyl.

59. The test element of claim 57, wherein $R^2$ is $C_1$–$C_6$ alkoxy or amino group $NR^3R^4$.

60. The test element of claim 57, wherein the compound is selected from the group consisting of N,N'-bis-(2-hydroxyethyl)-p-nitrosoaniline N,N'-dimethyl-p-nitrosoaniline N,N'-diethyl-p-nitrosoaniline N-methyl-N'-(4-nitrosophenyl)-piperazine N-(2-hydroxyethyl)-5-nitrosoindoline 2,4-dimethoxy-nitrosobenzene N,N'-bis-(2-methoxyethyl)-4-nitrosoaniline N-(4-nitrosophenyl)-morpholine N-(2,2-diethoxy-ethyl)N'-(4-nitrosophenyl)-piperazine p-nitrosophenol 3-methoxy-4-nitrosophenol.

61. The test element of claim 56, wherein the aromatic nitroso compound comprises a compound of formula II

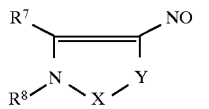

wherein

X—Y is NR$^5$—CO or N=CR$^6$

R$^5$ is selected from the group consisting of (a) hydrogen, (b) alkyl, which is unsubstituted or has a substituent selected from the group consisting of (1) hydroxy, (2) carboxy, (3) SO$_3$H, (4) PO$_3$H$_2$ and (5) dialkylphosphinyl, R$_6$ is selected from the group consisting of (a) hydrogen, (b) alkyl, (c) alkenyl, (d) alkoxy, (e) alkylthio, (f) aryl, (g) arylthio, (h) aralkyl, wherein each of (b)–(h) is unsubstituted or has a substituent selected from the group consisting of hydroxy, carboxy or a salt thereof, SO$_3$H or a salt thereof, PO$_3$H$_2$ or a salt thereof, and alkoxycarbonyl, (i) carboxy, (j) alkoxycarbonyl, (k) carboxyamido, (1) halogen, (m) amino which is unsubstituted or substituted by one or two alkyl residues which are unsubstituted or substituted by at least one residue selected from the group consisting of hydroxy, carboxy, and alkoxycarbonyl, wherein when amino is substituted by two alkyl residues, the two alkyl residues are unclosed or closed to from a ring that, in addition to the N atom of the amino group, is uninterrupted or interrupted by oxygen, sulphur or a further nitrogen atom, and (n) amino which is unsubstituted or substituted by up to two substituents, each independently selected from the group consisting of acyl, alkoxy, aralkoxycarbonyl, H$_2$N—CO, alkyl, aralkyl and arylcarbamoyl, R$^7$ is selected from the group consisting of (a) alkyl, (b) thioalkyl, (c) aralkyl, wherein each of (a)–(c) is unsubstituted or has a substituent selected from the group consisting of (1) hydroxy, (2) carboxy, (3) SO$_3$H and (4) PO$_3$H$_2$, and (d) amino which is unsubstituted or substituted by one or two alkyl groups, which alkyl groups are unsubstituted or have a substituent selected from the group consisting of (1) hydroxy, (2) carboxy, (3) SO$_3$H, (4) dialkylphosphinyl and (5) PO$_3$H$_2$, wherein at least one of R$^6$ and R$^7$ are an amino group and R$^8$ is alkyl or aralkyl, wherein R$^8$ is unsubstituted or has a substituent selected from the group consisting of hydroxy, carboxy, SO$_3$H and PO$_3$H$_2$, or wherein R$^7$ and R$^8$ together are a saturated or unsaturated chain having 3 or 4 members of nitrogen atoms or of carbon atoms, which saturated or unsaturated chain further contains zero or at least one nitrogen or sulphur atom, wherein the carbon atoms are unsubstituted or have a substituent selected from the group consisting of alkyl, alkoxy, alkylthio, hydroxy, aralkyl, aryl, carboxy, carboxamido, alkoxycarbonyl, cyano, halogen and amino, which amino is unsubstituted or substituted by one or two alkyl residues which are each unsubstituted or substituted by one or more substituents selected from the group consisting of (a) hydroxy, (b) carboxy, and (c) alkoxycarbonyl, wherein nitrogen atoms that are not bound via a double bond are substituted by alkyl or aralkyl, which alkyl or aralkyl are each independently unsubstituted or have a substituent selected from the group consisting of hydroxy, SO$_3$H, PO$_3$H$_2$, carboxy and dialkylphosphinyl, or two neighboring chain substituents form an alkylene group which is unsubstituted or substituted with aryl or is anellated, a tautomeric form or a salt thereof.

62. The test element of claim 61, wherein the aromatic nitroso compound comprises a compound selected from the group consisting of formulae III to XII

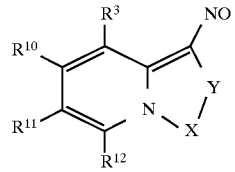

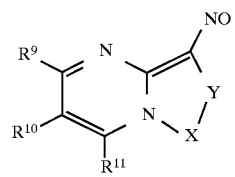

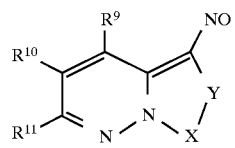

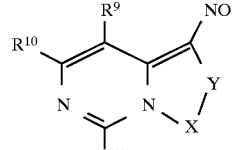

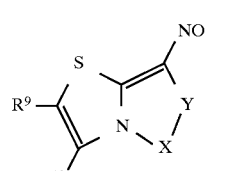

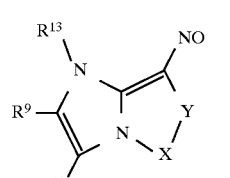

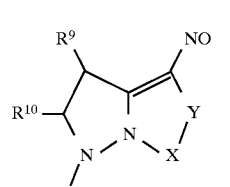

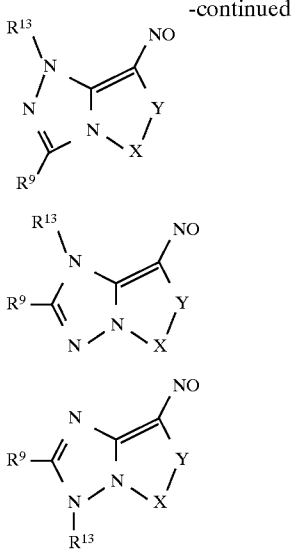

wherein
R⁹, R¹⁰, R¹¹ and R¹² are the same or different and each independently is selected from the group consisting of hydrogen, hydroxy, halogen, alkyl, akloxy, aklylthio, aralkyl, aryl, carboxy, alkoxycarbonyl, carboxamido, cyano, amino which is unsubstituted or substituted by one or two alkyl residues each of which is unsubstituted or substituted by at least one substituent selected from the group consisting of hydroxy, carboxy and alkoxycarbonyl, wherein two neighboring residues form an alkylene group which is unsubstituted or substituted by aryl or is anellated, and R¹³ is alkyl or aralkyl, each of which is unsubstituted or substituted by a substituent selected from the group consisting of hydroxy, carboxy, SO₃H, PO₃H₂ and dialkylphosphinyl.

63. The test element of claim 62, wherein the aromatic nitroso compound comprises a compound selected from the group consisting of formulae III, IV, V, VII, VIII and IX.

64. The test element of claim 62, wherein X—Y is N=CR⁶.

65. The test element of claim 57, wherein the aromatic nitroso compound is selected from the group consisting of 3-nitroso-2-methyl-pyrazolo-[1.5a]-pyridine,
3-nitroso-pyrazolo-[1.5a]-pyridine and
3-nitroso-pyrazolo [3.2-c]-s-triazole,
or a salt thereof.

66. The test element of claim 52, wherein in the substance BX, B comprises an aromatic compound and X comprises a substituent which is substituted or unsubstituted.

67. The test element of claim 66, wherein B comprises phenol or naphthol.

68. The test element of claim 66, wherein X comprises halogen or SO₃H.

69. The test element of claim 52, wherein BX comprises aniline or naphthylamine.

70. The test element of claim 52, wherein BX comprises 2,4,6-trihalogen-3-hydroxy-benzoic acid, 2,4-dihalogen-1-naphthol, 1-naphthol-4-sulfonic acid, 4-monohalogen-aniline, 4-monohalogen-phenol and 4-monohalogen-naphthol.

71. The test element of claim 52, wherein the chromogen A is present in a concentration of $10^{-3}$ to 1 mol/l.

72. The test element of claim 52, wherein the oxidizing enzyme is present in an amount of 0.1 to 100 U/test zone.

73. The test element of claim 52, wherein the substance BX is present in from a stoichiometric ratio to a 2-fold excess, compared to the chromogen A.

74. A test system for the simultaneous colorimetric and electrochemical measurement of an analyte, comprising
the test element of claim 52, in liquid contact with a sample liquid containing the analyte to form a liquid environment system; and
an electrode for electrochemically measuring the electrochemically measurable group X⁻, in liquid conductive contact with the liquid environment system.

* * * * *